United States Patent [19]

Strecker et al.

[11] Patent Number: 5,766,612
[45] Date of Patent: Jun. 16, 1998

[54] USE OF ENDGROUP-CAPPED FATTY AMIDE ALKOXYLATES

[75] Inventors: Beate Strecker, Ludwigshafen; Günter Oetter, Frankenthal; Alfred Oftring, Bad Dürkheim; Johannes Perner, Neustadt; Richard Baur, Mutterstadt; Volker Schwendemann, Neustadt; Martin aus dem Kahmen, Ludwigshafen; Wolfgang Reif, Frankenthal, all of Germany

[73] Assignee: BASF Aktiengesellschaft, Ludwigshafen, Germany

[21] Appl. No.: 632,436

[22] PCT Filed: Oct. 12, 1994

[86] PCT No.: PCT/EP94/03354

§ 371 Date: Apr. 22, 1996

§ 102(e) Date: Apr. 22, 1996

[87] PCT Pub. No.: WO95/11225

PCT Pub. Date: Apr. 27, 1995

[30] Foreign Application Priority Data

Oct. 22, 1993 [DE] Germany .................. 43 36 247.8

[51] Int. Cl.$^6$ .................................. C07C 233/18
[52] U.S. Cl. ................. 424/401; 510/535; 554/64; 554/69; 562/208; 562/224
[58] Field of Search ............. 554/64, 69; 564/208, 564/224; 424/401; 510/535

[56] References Cited

U.S. PATENT DOCUMENTS 3,180,786  4/1965  Domba et al. .................. 162/158
3,746,644  7/1973  Magne et al. .................. 508/249
4,624,803  11/1986  Balzer et al. .................. 252/527
5,124,079  6/1992  Smid et al. .................. 252/548

FOREIGN PATENT DOCUMENTS 161537     11/1985  European Pat. Off. .
B 211 493  6/1986   European Pat. Off. .
564402     10/1993  European Pat. Off. .
A 24 23 893 5/1974  Germany .
481633     1/1970   Switzerland .

*Primary Examiner*—Richard L. Raymond
*Attorney, Agent, or Firm*—Oblon, Spivak, McClelland, Maier & Neustadt, P.C.

[57] ABSTRACT

The use of endgroup-capped fatty amide alkoxylates I $$R^1\text{---CO---NH---}(CH_2)_n\text{---O---}(AO)_x\text{---}R^2 \quad (I)$$

where $R^1$ is $C_5$–$C_{21}$-alkyl or -alkenyl, $R^2$ is $C_1$–$C_4$-alkyl,

A is $C_2$–$C_4$-alkylene, n is 2 or 3, and x has a value from 1 to 6, as nonionic surfactants or emulsifiers in detergents, cleaners or body care compositions, as surface-active substances for industrial applications in electroplating, in the photographic industry, in petroleum production, in the pharmaceutical industry, in plant feeding and in crop protection formulations, and as surface-active substances in the production of emulsions and pigment and plastic dispersions.

10 Claims, No Drawings

USE OF ENDGROUP-CAPPED FATTY AMIDE ALKOXYLATES

This application is a 371 of PCT/EP94/03354, filed Oct. 12, 1994.

BACKGROUND OF THE INVENTION

1. Field of the Invention

The present invention relates to the use of endgroup-capped fatty amide alkoxylates of the general formula I $$R^1-CO-NH-(CH_2)_n-O-(AO)_x-R^2 \quad (I)$$

where $R^1$ is $C_5-C_{21}$-alkyl or -alkenyl, $R^2$ is $C_1-C_4$-alkyl,

A is $C_2-C_4$-alkylene, n is 2 or 3, and x has a value from 1 to 6, as nonionic surfactants or emulsifiers in detergents, cleaners or body care compositions, as surface-active substances for industrial applications in electroplating, in the photographic industry, in petroleum production, in the pharmaceutical industry, in plant feeding and in crop protection formulations, and as surface-active substances in the production of emulsions and pigment and plastic dispersions.

The invention furthermore relates to detergents, cleaners and body care compositions which contain the compounds I. Since some of the compounds I are novel substances, the invention also relates to these novel substances. The invention furthermore relates to a process for preparing these novel substances.

2. Discussion of the Background

Washing and cleaning processes in industry, commercial operations and domestically nowadays increasingly demand surface-active substances which are distinguished in particular by good alkali stability, a large reduction in surface tension and good wetting and foaming capacity, and for mechanical cleaning processes there is a need in particular for low foaming and efficient foam suppression. Furthermore, these surface-active substances ought to be substantially biodegradable and not entail any potential health risk.

DE-A 24 23 893 (1) describes a deicing and antiicing composition for aircraft which contains an addition of a water-dispersible compound of the formula α

$$R-X-(CH_2CH_2O)_n-Y \quad (\alpha)$$

where R is, inter alia, an unbranched or branched $C_{12}-C_{24}$-alkyl radical, X is, inter alia, the group —CO—NH—, n is a number from 1 to 30 and Y is, inter alia, a $C_1-C_{20}$-alkyl group. Another possible addition to this composition is a water-insoluble compound of the formula β

$$R^4-A-(CHR^1CH_2O)m-B \quad (\beta)$$

where $R^4$ is an unbranched or branched $C_8-C_{24}$-alkyl radical which may contain a hydroxyl group, A is, inter alia, the group —CO—NH—, $R^1$ is hydrogen or methyl, m is a number from 1 to 3 and B is, inter alia, a $C_1-C_5$-alkyl radical.

U.S. Pat. No. 3,746,644 (2) discloses oleic acid derivatives of the formula $$C_{17}H_{34}-CO-NH-(CH_2)_3-O-CH_2CH_2-O-CH_2CH_3$$

and $$C_{17}H_{34}-CO-NH-(CH_2)_3-O-CH_2CH_2-O-CH_2CH_2-O-CH_2CH_3.$$

These compounds are suitable as lubricants which withstand high pressures and are stable to bases.

EP-B 211 493 (3) relates to a liquid cleaner composition which comprises a mixture of an ionic surfactant and a polyalkoxy nonionic surfactant of the general formula RVEW. In this, R is an (ar)aliphatic hydrocarbon moiety, V is, inter alia, the group —CO—NH—, E is polyethoxy and/or polypropoxy (no general statement is made about the degree of alkoxylation, but it is 14 or 20 in the examples) and W is a nonionic endgroup, eg. OH or $CH_3$.

SUMMARY OF THE INVENTION

Said prior art fatty amide alkoxylates are, however, still in need of improvement in respect of their washing and cleaning properties. It is an object of the present invention to provide surfactants or emulsifiers for use in detergents, cleaners and body care compositions with an improved profile of properties.

We have found that this object is achieved by using the endgroup-capped fatty amide alkoxylates I defined at the outset for this purpose.

DETAILED DESCRIPTION OF THE PREFERRED EMBODIMENTS

The radical $R^1$ is $C_5-C_{21}$-alkyl or -alkenyl, preferably $C_7-C_{19}$-alkyl or -alkenyl, in particular $C_9-C_{17}$-alkyl or -alkenyl. $R^1$ is preferably the residue of a long-chain carboxylic acid, in particular of a naturally occurring fatty acid such as lauric acid, myristic acid, palmitic acid, stearic acid or oleic acid or of a carboxylic acid which has been synthesized by the oxo or Ziegler method. Mixtures of various $R^1$ radicals may also occur.

The radical $R^2$ is $C_1-C_4$-alkyl such as methyl, ethyl, n-propyl, isopropyl, n-butyl, isobutyl, sec-butyl or tert-butyl, preferably methyl, ethyl and n-butyl.

The variable A is, in particular, 1,2-alkylene groups, especially 1,2-ethylene, but also 1,2-propylene, 1,2-butylene or 2,3-butylene.

The degree of alkoxylation x has a value from 1 to 6, preferably from 2.2 to 4.5, in particular from 2.5 to 4, where x can be a statistical average, ie. the maximum frequency in a distribution plot.

A particularly preferred embodiment comprises the use of endgroup-capped fatty amide alkoxylates I where $R^1$ is $C_7-C_{19}$-alkyl or -alkenyl, $R^2$ is methyl, ethyl or n-butyl, A is 1,2-ethylene, n is 2 or 3, and x has a value from 2.2 to 4.5.

The compounds I are suitable as nonionic surfactants in solid or liquid cleaners for industry, catering and domestically, in particular for cleaning hard surfaces, for example made of glass, porcelain, ceramic or metal, for example in manual dishwashing compositions. The compounds I are also very suitable for mechanical cleaning processes in the metal, papermaking, textile and foodstuffs industries, for example for industrial bottlewashing or mechanical dishwashing.

Highly alkaline cleaners are used for cleaning bottles in the beverage industry. The alkali dissolves, neutralizes or hydrolyzes beverage residues and converts the label gum into a highly foaming water-soluble form. All these processes take place with high mechanical input and thus favor the foaming suitability, which is anyway great, of starch and sugar breakdown products.

Another application relates to industrial cleaning processes in the metal industry. In this case too, a very efficiently wetting alkaline aqueous solution is used as cleaning medium under high pressure to remove drawing and rolling greases and carboxyl-containing organic corrosion inhibitors. In this case, the surfactants used according to the invention are intended not only to improve the wetting properties but, in particular, also to contribute to foam suppression of, for example, anionic surfactants of the alkylbenzenesulfonate type and other sulfo- and carboxyl-containing surfactants.

The compounds I are likewise suitable in an excellent manner as nonionic surfactants in solid or liquid textile detergent compositions. In this case it is possible for advantageous synergistic effects to be achieved in combination with conventional anionic and/or nonionic surfactants.

The compounds I may furthermore be used very successfully in cosmetics as emulsifiers in body care compositions such as skin creams, lotions, gels, skin oils or hair shampoos. The compounds I are generally suitable as surface-active substances for industrial applications and thus have a large number of other possible industrial uses. Possible areas of use in this connection are electroplating, the photographic industry, petroleum production, the pharmaceutical industry, plant nutrition and crop protection; the compounds I are generally suitable for active substance compositions comprising hydrophobic and hydrophilic components.

The compounds I can also be used very successfully as emulsifiers or stabilizers in the production of emulsions and pigment and plastic dispersions.

The present invention furthermore relates to detergents, cleaners and body care compositions which, besides the ingredients customary for these purposes, contain from 0.1 to 50% by weight, preferably 1 to 30% by weight, based on the total amount of the composition, of one or more compounds I. The ingredients and the composition of such detergents, cleaners and body care compositions are known to the skilled worker and therefore need not be explained in detail here.

The endgroup-capped fatty amide alkoxylates I are stable to hydrolysis in alkaline and weakly acidic medium and are distinguished by their good use properties such as efficient reduction in surface tension, good wetting capacity, good foaming capacity for some of the compounds I and low foaming and good foam suppression for other compounds I, good stability in hard water and good detergency with, at the same time, biodegradability and toxicological acceptability.

The present invention also relates to endgroup-capped fatty amide alkoxylates of the general formula Ia $$R^1—CO—NH—(CH_2)_n—O—(AO)_y—R^2 \quad (Ia)$$

where $R^1$ is $C_5$–$C_{21}$-alkyl or -alkenyl, $R^2$ is $C_1$–$C_4$-alkyl,

A is $C_2$–$C_4$-alkylene, n is 2 or 3, and y has a value from greater than 2 to 6, preferably from 2.2 to 4.5, in particular from 2.5 to 4.

The compounds Ia, as well as the compounds I, can be prepared in an advantageous manner by reacting fatty acid esters of the general formula II $$R^1—CO—O—R^3 \quad (II)$$

where $R^3$ is $C_1$–$C_8$-alkyl, in particular $C_1$–$C_4$-alkyl, and $R^1$ has the abovementioned meaning, with polyoxyalkylene amines of the general formula III $$H_2N—(CH_2)_n—O—(AO)_y—R^2 \quad (III)$$

where $R^2$, A, n and y have the abovementioned meanings. This is usually carried out in the presence of basic catalysts, preferably alkali metal alcoholates.

The compounds Ia can also be prepared in an advantageous manner by reacting fatty acids of the general formula IV $$R^1—COOH \quad (IV)$$

where $R^1$ has the abovementioned meaning, with the polyoxyalkylene amines III. Acidic catalysts are usually employed for this, preferably mineral acids such as hydrochloric acid, sulfuric acid or phosphoric acid, carboxylic acids such as formic acid or acetic acid or sulfonic acids, which may also have surfactant properties, such as p-toluenesulfonic acid or dodecylbenzenesulfonic acid.

Corresponding compounds I are prepared by reacting polyoxyalkylene amines of the general formula $$H_2N—(CH_2)_n—O—(AO)_x—R^2.$$

PREPARATION EXAMPLES

EXAMPLE 1

102.5 g (0.5 mol) of n-butyltriglycolamine of the formula $$H_2N—(CH_2CH_2O)_3—C_4H_9$$

were introduced into a glass reactor and heated to 100° C. While stirring, 110 g (0.5 mol) of methyl dodecanoate were added dropwise over the course of 20 minutes. The reaction mixture was heated to 120° C. and, at this temperature, 13.5 g (corresponding to 0.075 mol of NaOCH$_3$) of a sodium methanolate solution (30% by weight in methanol) were slowly added dropwise, and the mixture was stirred at 120° C. for 15 minutes. The pressure was then slowly reduced to 80–100 mbar. After stirring at 120° C. and 80–100 mbar for 3 hours, a further 4.5 g of the sodium methanolate solution were added and the reaction mixture was then stirred at 120° C. and 80–100 mbar for 2 hours. The completeness of conversion was checked by infrared spectroscopy.

The result was 201 g of a pale brown solid which was waxy at room temperature.

EXAMPLE 2

The reaction was carried out as in Example 1 starting from 103.5 g (0.5 mol) of methyltetraglycolamine of the formula $$H_2N—(CH_2CH_2O)_4—CH_3$$

and 110 g (0.5 mol) of methyl dodecanoate.

The result was 198 g of a pale brown product which was waxy at room temperature.

EXAMPLE 3

The reaction was carried out as in Example 1 starting from 110.5 g (0.5 mol) of ethyltetraglycolamine of the formula $$H_2N—(CH_2CH_2O)_4—C_2H_5$$

and 110 g (0.5 mol) of methyl dodecanoate.

The result was 200 g of a pale brown product which was waxy at room temperature.

EXAMPLE 4

The reaction was carried out as in Example 1 starting from 81.5 g (0.5 mol) of methyltriglycolamine of the formula

$$H_2N-(CH_2CH_2O)_3-CH_3$$

and 110 g (0.5 mol) of methyl dodecanoate.

The result was 175 g of a pale brown product which was waxy at room temperature.

EXAMPLE 5

The reaction was carried out as in Example 1 starting from 88.5 g (0.5 mol) of ethyltriglycolamine of the formula

$$H_2N-(CH_2CH_2O)_3-C_2H_5$$

and 110 g (0.5 mol) of methyl dodecanoate.

The result was 184 g of a pale brown product which was waxy at room temperature.

EXAMPLE 6

The reaction was carried out as in Example 1 starting from 110.9 g (0.5 mol) of ethyltetraglycolamine of the formula

$$H_2N-(CH_2CH_2O)_4-C_2H_5$$

and 114.0 g (0.5 mol) of a commercial mixture of saturated $C_8-C_{18}$-fatty acid methyl esters.

The result was 189 g of a pale brown product which was waxy at room temperature.

EXAMPLE 7

The reaction was carried out as in Example 1 starting from 73.2 g (0.4 mol) of a polyoxyalkylene amine of the formula

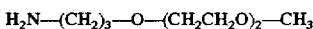
$$H_2N-(CH_2)_3-O-(CH_2CH_2O)_2-CH_3$$

and 89.8 g (0.4 mol) of methyl dodecanoate.

The result was 152 g of a pale brown product which was waxy at room temperature.

EXAMPLE 8

51.8 g (0.25 mol) of methyltetraglycolamine of the formula

$$H_2N-(CH_2CH_2O)_4-CH_3$$

were introduced into a glass reactor and heated to 100° C. While stirring, 51.8 g (0.25 mol) of coconut fatty acid (Edenor® K8-18 from Henkel) were added over the course of 20 minutes. The reaction mixture was then heated to 120° C. and, at this temperature, 1.0 g (0.003 mol) of dodecylbenzenesulfonic acid were slowly added, and the mixture was heated to 180° C. After stirring at 180° C. for 3 hours, the remaining water of reaction was removed by distillation under 80 to 100 mbar. After this, infrared spectroscopy showed that the reaction mixture no longer contained carboxylic acid. The contents of the reactor were discharged at 80° to 100° C.

The result was 94.8 g of a solid which was waxy at room temperature.

Use Examples

The cloud point was determined by the DIN 53917 method.

The foaming capacity was tested by the DIN 53902 method at 40° C. with 2 g/l test substance and a water hardness of 1.78 mmol Ca/l (≙10° German hardness). This entailed determination of the foam volume in ml 30 sec after cessation of foam generation.

For further characterization, the wetting capacity was tested by immersing a cotton fabric in the surfactant solution to be investigated as specified in DIN 53901. The measurement was carried out with 2 g/l test substance and 2 g/l sodium carbonate in distilled water at 20° and 70° C. This entailed measurement of the time in sec after which the fabric loses its buoyancy caused by the entrapped air and starts to sink. A shorter time means a better wetting capacity.

The surface tension was measured by the DIN 53914 method at 20° C. with 0.1 g/l test substance. This entailed measurement of the force in mN/m which is necessary to pull a horizontally suspended ring out of the surface of the liquid.

The foam suppression capacity was tested by the "egg test" in a dishwashing machine. This entailed determination, by magnetic induction measurement with the aid of a counter, of the revolutions of a spray arm in a commercially available domestic automatic dishwasher. The revolutions of the spray arm are reduced by foam formation which occurs in particular in the presence of proteins (egg white). The revolutions thus represent, because of the reduced force of repulsion, a measure of the suitability of surfactants in cleaning equipment with high mechanical input. The test lasted 12 minutes, and the average revolutions were calculated from the total revolutions. The washing process was started at room temperature, and the temperature of the rinsing water after about 10 minutes was 60° C.

The following table shows the results of the measurements.

| Product of Example No. | Cloud point [°C.] | Foam capacity [ml] | Wetting capacity 20° C. [sec] | Wetting capacity 70° C. [sec] | Surface tension [mN/m] | "Egg test" [rpm] |
|---|---|---|---|---|---|---|
| 1 | 0 | 0 | 96 | 175 | 33.4 | 112 |
| 2 | 58 | 340 | 8 | 22 | 31.9 | 44 |
| 3 | 36 | 30 | 22 | 43 | 29.8 | 84 |
| 4 | 55 | 85 | 28 | 32 | 28.8 | 50 |
| 5 | 30 | 10 | 68 | 48 | 32.1 | 81 |
| 6 | 61 | 20 | 17 | 30 | 28.7 | 110 |
| 7 | 0 | 10 | 69 | 45 | 31.9 | 82 |
| for comparison: | | | | | | |
| A | 100 | 280 | >300 | >300 | 37.6 | 20 |
| B | 99 | 140 | >300 | 272 | 50.4 | 43 |
| C | 64 | 10 | 140 | 91 | 40.9 | 34 |

The comparison substance were nonionic surfactants disclosed in (3) of the formula

$$C_{11}/C_{13}\text{-alkyl-CO-NH-}(CH_2CH_2O)_{20}-W$$

where W=OH (Example A), $CH_3$ (Example B) or n—$C_4H_9$ (Example C).

As is evident from the examples, the substances according to the invention show distinctly more favorable properties than the comparison substances.

Examples 2 and 4 show products which can be used in textile detergents or manual dishwashing compositions.

Compared with comparisons A and B, the substances according to the invention show a distinctly better reduction in surface tension and a distinctly better wetting capacity.

Examples 1, 3, 5, 6 and 7 show substances suitable for industrial cleaners (mechanical cleaning operations). Besides their low foaming, these substances show a greater reduction in surface tension, a better wetting capacity and, particularly importantly, a distinctly better foam suppression in the dishwashing machine test than, for example, comparison substance C.

We claim:

1. A method of improving the surfactant properties of a composition, comprising adding to a composition a compound of the formula (I)

$$R^1\text{—CO—NH—}(CH_2)_n\text{—O—}(AO)_x R^2 \quad (I)$$

wherein $R^1$ is $C_7$–$C_{21}$-alkyl or $C_7$–$C_{21}$-alkenyl, $R^2$ is $C_1$–$C_4$-alkyl, A is $C_2$–$C_3$-alkylene, n is 2 or 3, and x has a value from 2 to 6.

2. The method of claim 1, wherein:

$R^1$ is $C_7$–$C_{19}$-alkyl or $C_7$–$C_{19}$-alkenyl, $R^2$ methyl, ethyl or n-butyl, A is 1,2-ethylene, n is 2 or 3, and x has a value from 2.2 to 4.5.

3. A compound of formula (Ia):

$$R^1\text{—CO—NH—}(CH_2)_n\text{—O—}(AO)_y R^2 \quad (Ia)$$

wherein $R^1$ is $C_7$–$C_{21}$-alkyl or $C_7$–$C_{21}$-alkenyl, $R^2$ is $C_1$–$C_4$-alkyl, A is $C_2$–$C_3$-alkylene, n is 2 or 3, and y has a value of from greater than 2 to 6.

4. The compound of claim 3, wherein:

$R^1$ is $C_7$–$C_{19}$-alkyl or $C_7$–$C_{19}$-alkenyl, $R^2$ methyl, ethyl or n-butyl, A is 1,2-ethylene, n is 2 or 3, and y has a value from 2.2 to 4.5.

5. A detergent, cleaner, or body care composition which, besides conventional ingredients, comprises from 0.1 to 50 % by weight of a compound of formula (I):

$$R^1\text{—CO—NH—}(CH_2)_n\text{—O—}(AO)_x R^2 \quad (I)$$

wherein $R^1$ is $C_7$–$C_{21}$-alkyl or $C_7$–$C_{21}$-alkenyl, $R^2$ is $C_1$–$C_4$-alkyl, A is $C_2$–$C_3$-alkylene, n is 2 or 3, and x has a value from 2 to 6.

6. The composition of claim 5, wherein:

$R^1$ is $C_7$–$C_{19}$-alkyl or $C_7$–$C_{19}$-alkenyl, $R^2$ methyl, ethyl or n-butyl, A is 1,2-ethylene, n is 2 or 3, and x has a value from 2.2 to 4.5.

7. A process for preparing a compound of formula (Ia):

$$R^1\text{—CO—NH—}(CH_2)_n\text{—O—}(AO)_y R^2 \quad (Ia)$$

wherein $R^1$ is $C_7$–$C_{21}$-alkyl or $C_7$–$C_{21}$-alkenyl, $R^2$ is $C_1$–$C_4$-alkyl, A is $C_2$–$C_3$-alkylene, n is 2 or 3, and y has a value of from greater than 2 to 6, said process comprising:

(i) reacting a compound of formula (II)

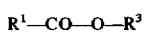
$$R^1\text{—CO—O—}R^3 \quad (II)$$

wherein $R^3$ is $C_1$–$C_8$-alkyl and $R^1$ is as defined above with a compound of formula (III)

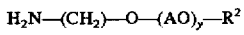
$$H_2N\text{—}(CH_2)\text{—O—}(AO)_y\text{—}R^2 \quad (III)$$

wherein $R^2$, A, n, and y are as defined above.

8. The process of claim 7, $R^1$ is $C_7$–$C_{19}$-alkyl or $C_7$–$C_{19}$-alkenyl, $R^2$ methyl, ethyl or n-butyl, A is 1,2-ethylene, n is 2 or 3, and y has a value from 2.2 to 4.5.

9. A process for preparing a compound of formula (Ia):

$$R^1\text{—CO—NH—}(CH_2)_n\text{—O—}(AO)_y R^2 \quad (Ia)$$

wherein $R^1$ is $C_7$–$C_{21}$alkyl or $C_7$–$C_{21}$-alkenyl, $R^2$ is $C_1$–$C_4$-alkyl, A is $C_2$–$C_3$-alkylene, n is 2 or 3, and y has a value from greater than 2 to 6, said process comprising:

(i) reacting a compound of formula (IV)

$$R^1\text{—COOH} \quad (IV)$$

wherein $R^1$ is as defined above with a compound of formula (III)

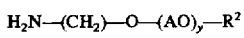
$$H_2N\text{—}(CH_2)\text{—O—}(AO)_y\text{—}R^2 \quad (III)$$

wherein $R^2$, A, n, and y are as defined above.

10. The process of claim 9, $R^1$ is $C_7$–$C_{19}$-alkyl or $C_7$–$C_{19}$-alkenyl, $R^2$ methyl, ethyl or n-butyl, A is 1,2-ethylene, n is 2 or 3, and y has a value from 2.2 to 4.5.

* * * * *